United States Patent [19]

Lotman

[11] Patent Number: 5,016,268
[45] Date of Patent: May 14, 1991

[54] PATIENT SUPPORT

[76] Inventor: D. Barry Lotman, 13175 Sand Grouse Ct., Palm Beach Gardens, Fla. 33480

[21] Appl. No.: 418,145

[22] Filed: Oct. 6, 1989

Related U.S. Application Data

[63] Continuation-in-part of Ser. No. 144,469, Jan. 15, 1988.

[51] Int. Cl.$^5$ .......................... H05G 1/02; A61B 6/04; A61B 6/14; A61G 7/08
[52] U.S. Cl. ..................... 378/177; 378/195; 378/209; 378/20; 378/68; 378/170; 5/81 R; 5/11; 5/63; 5/60
[58] Field of Search ............... 378/177, 170, 195, 208, 378/209, 20, 68; 5/81 R, 11, 63, 60

[56] References Cited

U.S. PATENT DOCUMENTS

| 595,734 | 12/1897 | Rand et al. |
| 2,245,909 | 10/1937 | Enfiajian |
| 3,535,719 | 10/1970 | Murcott |
| 3,717,885 | 5/1971 | De Mare ........................ 5/81 R |
| 3,775,781 | 12/1973 | Bruno et al. ...................... 5/81 R |
| 3,795,021 | 3/1974 | Moniot |
| 3,935,604 | 2/1976 | Collins |
| 4,024,861 | 3/1977 | Vincent |
| 4,175,297 | 11/1979 | Robbins et al. |
| 4,190,286 | 2/1980 | Bentley |
| 4,524,762 | 6/1985 | Schulman ......................... 5/60 |
| 4,617,690 | 10/1986 | Grebe |
| 4,745,647 | 5/1988 | Goodwin |
| 4,760,615 | 8/1988 | Furniss ............................ 5/81 R |
| 4,873,710 | 10/1989 | Lotman ............................ 378/177 |

FOREIGN PATENT DOCUMENTS

| 0222672 | 5/1987 | European Pat. Off. |
| 0292218 | 11/1988 | European Pat. Off. |
| 2522863 | 11/1976 | Fed. Rep. of Germany |
| 2816641 | 10/1978 | Fed. Rep. of Germany |
| 1487809 | 7/1967 | France |
| 2377795 | 8/1978 | France |
| 2169195 | 7/1986 | United Kingdom |

Primary Examiner—Edward P. Westin
Assistant Examiner—Don Wong
Attorney, Agent, or Firm—Eckert Seamans Cherin & Mellott

[57] ABSTRACT

A patient support includes a support surface and lifting structure adapted to permit the insertion of an x-ray cassette beneath the portion of the patient's body that is to be x-rayed. The structure for lifting preferably includes a plurality of inflatable runners. Structure for selectively deflating the runners is provided so as to permit insertion of an x-ray cassette between adjacent runners and beneath the patient. Structure for placing the inflatable runners in fluid connection with fluid supply means is provided such that the runners can be reinflated. In an alternative embodiment, the inflatable runners can be replaced by mechanical lifting apparatus.

25 Claims, 4 Drawing Sheets 5,016,268

PATIENT SUPPORT

CROSS REFERENCE TO RELATED APPLICATIONS

This is a continuation-in-part application of Applicant's co-pending application Ser. No. 144,469, filed Jan. 15, 1988.

BACKGROUND OF THE INVENTION

1. Field of the Invention

This invention relates generally to medical equipment, and more particularly to patient supports for use in medical facilities.

2. Description of the Prior Art

Bedridden hospital patients must sometimes be x-rayed and it is necessary to place an x-ray cassette beneath the body part that is to be x-rayed. This requires attendants to lift the patient's entire body, or at least the part of the body to be x-rayed, from the patient support. Some patients, particularly those in trauma situations, should not be moved or, if movement is absolutely necessary, must be moved with great care to avoid further injury and discomfort to the patient. It is difficult to manually move and x-ray a patient without jarring or otherwise disturbing the patient.

SUMMARY OF THE INVENTION

It is an object of the invention to provide a patient support which will permit the insertion of an x-ray cassette beneath the patient.

It is another object of the invention to provide a patient support which will not disturb the patient.

It is yet another object of the invention to provide a patient support which will permit the insertion of an x-ray cassette under virtually any portion of the patient's body.

These and other objects are accomplished by a patient support for a patient comprising a support portion with lifting means positioned about the support portion and adapted for movement so as to permit the insertion of an x-ray cassette beneath the portion of the patient's body that is to be x-rayed. The lifting means preferably comprises a plurality of inflatable runners. Means for placing the inflatable runners in fluid connection with fluid supply means are provided so that the runners can be inflated and the patient is lifted. Structure for the selective deflation of the runners is also provided. The runners are spaced apart from one another and adapted, when deflated, to permit the insertion of an x-ray cassette beneath a corresponding portion of the patient.

The runners are preferably substantially parallel to one another and laterally aligned on the support portion so as to be substantially parallel with the axis of the shoulders of the patient. The x-ray cassette can thereby be inserted from along the side of the patient and positioned between adjacent runners at a plurality of locations relative to the body of the patient.

The means for placing the inflatable runners in fluid connection with the fluid supply means preferably comprises a manifold which forms a passage for fluid between the fluid supply means and the interior spaces of the hollow runners. Valves are preferably located in lines connecting the manifold to the various runners. The runners can thereby be inflated, and selectively deflated so as to permit the insertion of an x-ray cassette beneath the corresponding portion of the patient's body that will be x-rayed.

The valves are preferably three position valves providing a closed condition, an inflating condition, and an exhaust condition. The exhaust condition permits the fluid to escape and thus deflate the runner. Fluid can be permitted to escape to the atmosphere if it is a gas and is not harmful, or can be returned to a fluid storage tank through suitable conduit means. Electric control can be provided so that the patient support of the invention can be operated without necessity of manually turning valves. The valves can be made operable by electric solenoids. The electric solenoids are preferably operable to position the valves in either of the three positions. A control panel can be provided so that the operator does not have to walk around the table to activate the solenoids.

The runners preferably are fixed directly to a surface of the support portion. The runners can be made from any suitable material, but preferably are formed from a flexible material that collapses when deflated to provide as plane a surface as possible for insertion of the x-ray cassette. The runners can be fixed in concave depressions formed in the support surface so that the accumulated runner material, when deflated, falls within the cavity and does not create an obstruction for insertion of the x-ray cassette.

In an alternative embodiment, the patient support comprises two parts including a lower, base portion, and an upper, support portion. The support portion includes the support surface for the patient and is spaced from the base portion by a plurality of inflated cells. The inflated cells are preferably fixed to the base portion. The cells can be selectively deflated to permit the insertion of an x-ray cassette between the base portion and the support portion, and to thereby permit an x-ray to be taken of a corresponding portion of the patient's body. In another embodiment, a plurality of inflatable runners are provided substantially between the base portion and the support portion. The runners can be selectively inflated to lift a corresponding portion of the support portion from the base portion, and are spaced apart from one another so as to permit the insertion of an x-ray cassette therebetween. It is also possible to use mechanical drive means to lift the support portion from the base portion to permit the insertion of the x-ray cassette.

BRIEF DESCRIPTION OF THE DRAWINGS

There are shown in the drawings embodiments which are presently preferred, it being understood that the invention is not limited to the precise arrangements and instrumentalities shown, wherein.

DETAILED DESCRIPTION OF THE PREFERRED EMBODIMENTS

Figure 1:
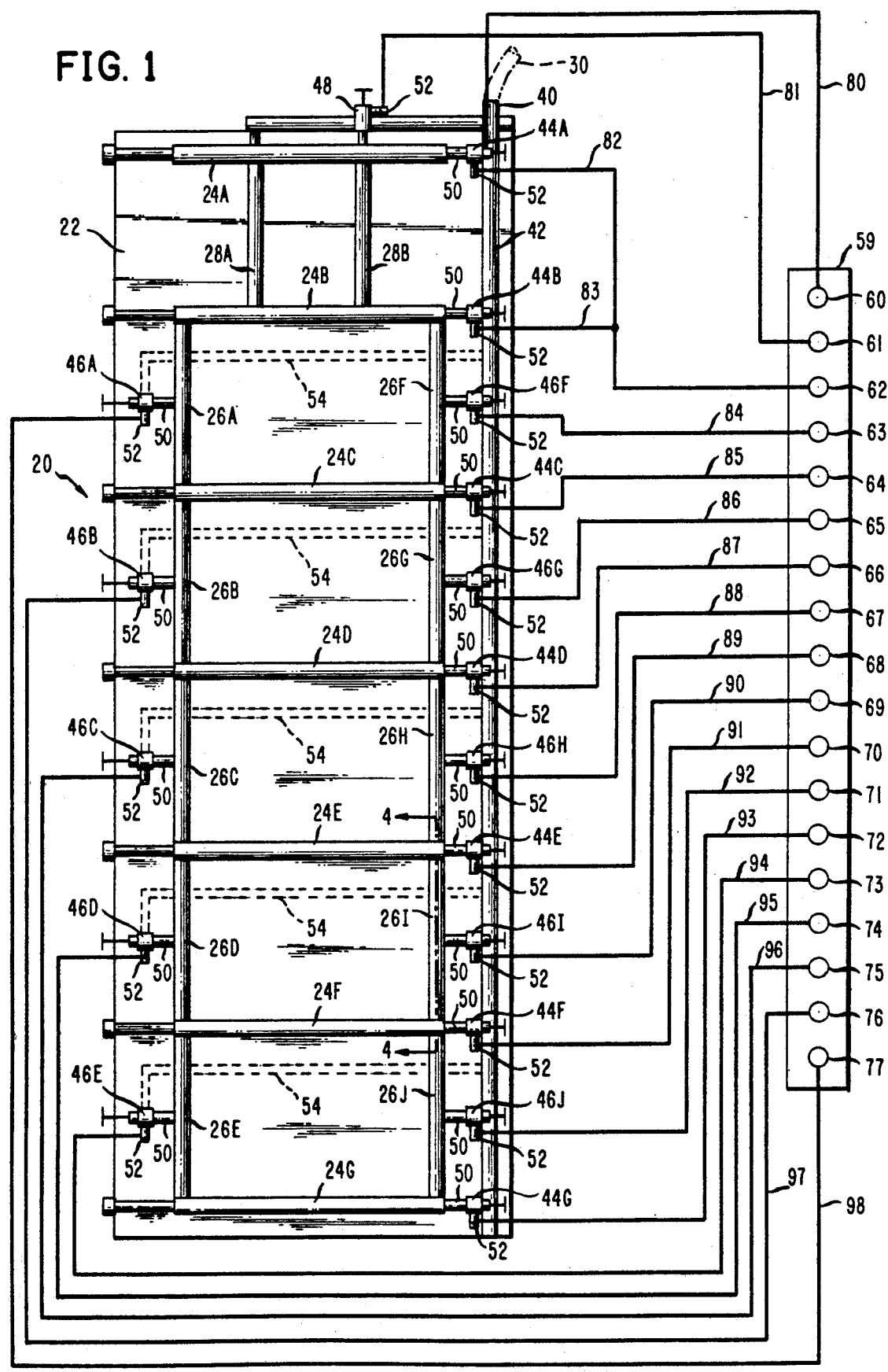
FIG. 1 is a plan view, partially in phantom, of a patient support according to the invention, and with controls shown in schematic form.
Figure 2:
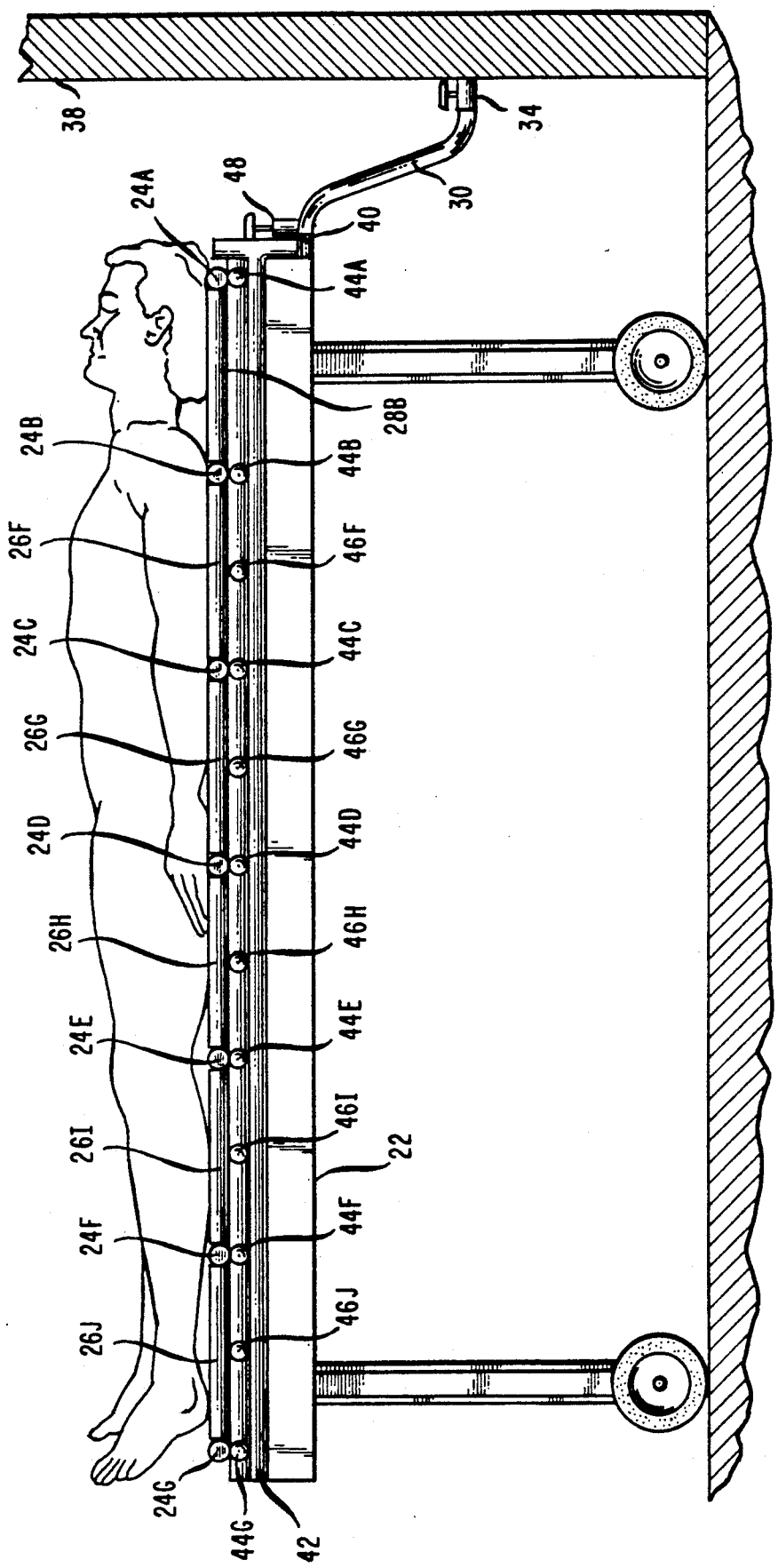
FIG. 2 is a side elevation in a first mode of operation.
Figure 3:
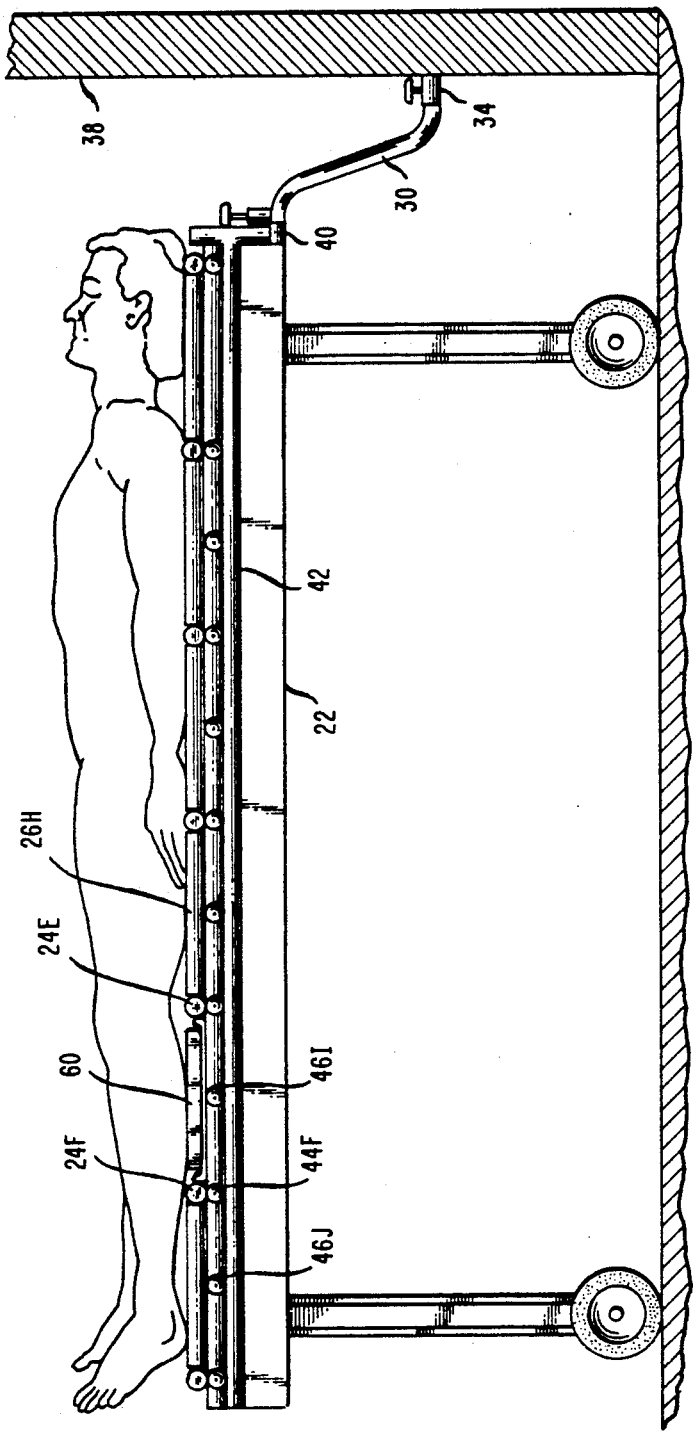
FIG. 3 is a side elevation in a second mode of operation.
Figure 5:
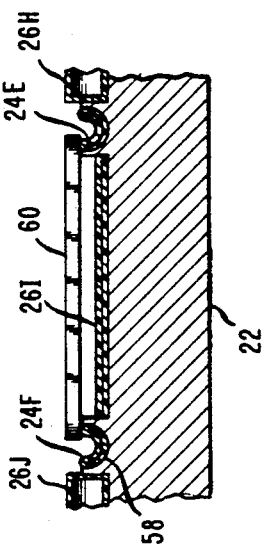
FIG. 5 is a cross-section taken along line 4—4 in FIG. 1 and in an alternative mode of operation.

Features and advantages of this invention are described in Applicant's co-pending application Ser. No. 144,469, to be U.S. Pat. No. 4,873,710. The disclosure of this application and patent are hereby incorporated fully by reference. The application discloses a patient support which has particular utility for taking x-ray images of patients. Typically, these patients must be lifted or otherwise moved to permit placement of an x-ray cassette beneath a corresponding portion of the patient's body that is to be x-rayed. The invention described in Applicant's co-pending application utilizes inflatable runners to lift corresponding portions of the patient's body, and to thereby permit insertion of the x-ray cassette without jarring movement of the patient.

The present invention provides alternative means for insertion of the x-ray cassette. In FIGS. 1-5 there is shown a patient support 20 having a support portion 22 which can be formed similarly to traditional hospital mattresses and, thus, can be constructed of foam or the like. The support portion 22 can be of variable dimension, but current emergency room supports are approximately 24×72 inches in dimension. A number of inflatable runners are provided on the surface of the support portion 22. These runners are spaced apart from one another and adapted, when inflated, to lift an adjacent portion of the patient. The number and position of the runners can be varied, but it is preferred to provide several lateral runners 24A-G as shown. A plurality of longitudinal runners 26A-J are provided so as, when inflated, to fully support the patient over the support portion 22. Longitudinal head support runners 28A-B can also be provided. It will be understood that more or fewer runners, and in different orientations, could also be provided so long as the runners adequately support the patient.

The runners are inflated by a supply of suitable fluid. The fluid can be a liquid such as water or oil, but preferably is a gas. The gas can be provided from a fluid supply means adapted specifically for this purpose, but preferably means are provided for connecting the runners to the oxygen supply lines in existence in most emergency and operating rooms. This connection can be an elastomeric hose 30 which fits onto an oxygen outlet such as the wall mounted nozzle 34 extending outwardly from the wall 38. The flexible hose 30 is connected to a valve 40. The valve 40 is preferably connected to a manifold 42 which distributes the fluid to the various runners. The manifold 42 can be conveniently fixed to a side of the patient support 22 by suitable fastening means or straps.

It is preferable to provide means for selectively deflating the runners so that only those runners that underlie the portion of the body that must be x-rayed are deflated. This will permit the insertion of an x-ray cassette beneath the corresponding portion of the body. Selective deflation can be accomplished by providing valves in the fluid flow lines to the individual runners. Valves 44A-G can be provided in the fluid flow lines to the runners 24A-G, respectively. Valves 46A-J can be provided in the fluid flow lines to the runners 26A-J, respectively. An additional valve 48 controls inflation of the head support runners 28A-B. A preferable position for the valves 44A-G, 46A-J, and 48 is in the connection lines 50, upstream from the runners or as shown at the juncture of the connection lines with the manifold 42. Connection lines 54 (phantom lines in FIG. 1) can extend underneath, or through, the support portion 22 to supply fluid to valves 46A-E.

The valves can be of suitable construction known in the art for this purpose, but preferably are three position valves which provide a closed condition, an open and thus inflation condition, and an exhaust or deflation condition. The deflation condition permits fluid to escape and thus collapse the runner. Fluid can be permitted to escape to the atmosphere if it is a harmless gas, or it ca be returned to a fluid storage tank by the incorporation of suitable conduit structure.

Figure 4:
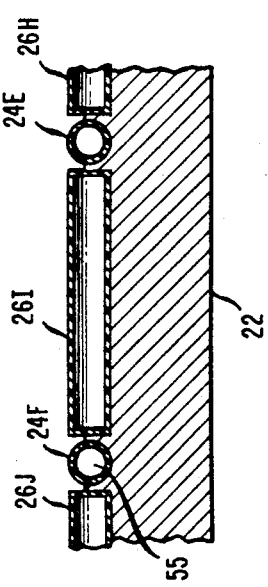
FIG. 4 is a cross-section taken along line 4—4 in FIG. 1.

The runners are preferably formed from fluid-tight flexible tubes that can be inflated by introducing the fluid into the hollow core 55 of the runners (FIG. 4). It is desirable to fix the runners in a concave seat 58 formed in the support surface 22. The flexible tube material will gather in the depression when the fluid pressure is removed instead of gathering on the surface of the patient support, so that the presence of the material will not interfere with insertion of an x-ray cassette 60 (FIG. 4).

Electric control of the valves can be provided. This can be accomplished by the provision of an electric solenoid 52 for each of the valves 44A-G, 46A-J and 48. The solenoids 52 operate to actuate the three position valves 44A-G, 46A-J and 48. Control of the solenoids 52 can conveniently be located in a control panel 59. The control panel 59 has a plurality of switch means 60-77. The switch means are operable to activate the solenoids 52 to inflate selected runners through a plurality of electric control paths 80-98. The switch means 60-77 are operable to energize control paths 80-98 in a manner suited to permit control of the solenoids 52 and selected operation of the valves 44A-G, 46A-J and 48 to selectively control inflation and deflation. Deflation of the runners will permit the insertion of the cassette 60 in an appropriate position underlying a portion of the body of the patient that is to be x-rayed.

Figure 6:
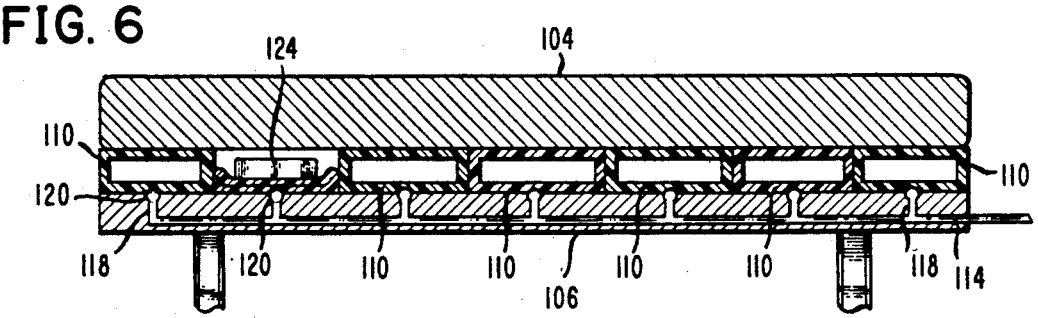
FIG. 6 is a cross-section of a first alternative embodiment.

Other embodiments are possible. There is shown in FIG. 6, for example, a patient support with a support portion 104 and a base portion 106. Means are provided for selectively lifting the support portion 104 from the base portion 106. The lifting means can be a plurality of inflatable runners 110 positioned between the support portion 104 and the base portion 106, and preferably are fixed to the base portion 106. The inflatable runners 110 are adapted, in the inflated condition, to lift the support portion 104 from the base portion 106. An air supply manifold 114, connecting lines 118, and control valves 120 can be provided as previously described. The valves 120 can be manipulated by suitable control means, either manual or automated, to selectively deflate one or more of the inflatable runners 110 to permit insertion of an x-ray cassette 124.

Figure 7:
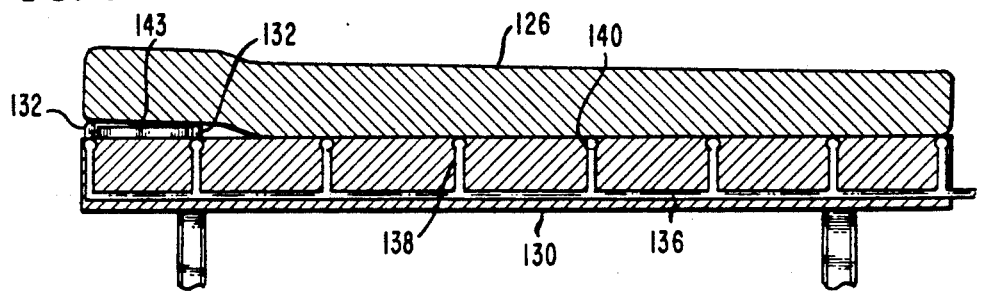
FIG. 7 is a cross-section of a second alternative embodiment.

In FIG. 7 there is shown another embodiment, which also comprises an upper, support portion 126 and a base portion 130. A plurality of inflatable runners 132 are disposed between the support portion 126 and the base portion 130, and are preferably provided on an upper surface of the base portion 130 as shown. A fluid supply manifold 136 can be used to supply fluid to a plurality of connection lines 138 and valves 140, to supply fluid to the inflatable runners 132. The valves 140 can be selectively controlled, either manually or by automation, to selectively inflate the runners 132. The inflatable runners 132 are spaced apart from one another a distance adapted to permit the insertion of an x-ray cassette 143. Selective inflation of the runners 132 lifts a corresponding portion of the support portion 126 from the base portion 130, and permits the insertion of an x-ray cassette 143 between the inflated runners 132 for the x-raying of a corresponding portion of the patient's body on the support portion 126.

Figure 8:
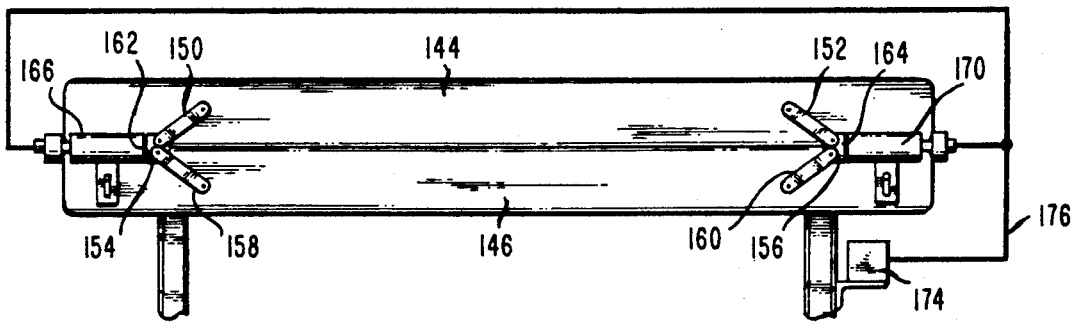
FIG. 8 is a side elevation, partially in schematic, of a third alternative embodiment, and in a first mode of operation.
Figure 9:
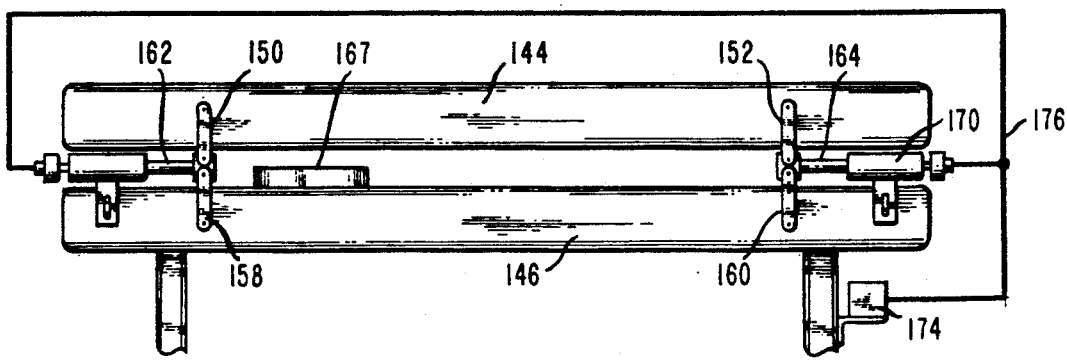
FIG. 9 is a side elevation, partially in schematic, of the third embodiment of FIG. 8, and in an alternative mode of operation.

A mechanical embodiment of the invention is depicted in FIGS. 8-9. The mechanical embodiment includes an upper, support portion 144 and a lower, base portion 146. Arms 150, 152 are pivotally mounted to the support portion 144 and to connecting members 154, 156. Arms 158, 160 are pivotally mounted to the lower, base portion 146 and to the connecting members 154, 156, respectively. The connecting members 154, 156 are fixed to shafts 162, 164 of solenoids 166, 170, respectively. Operation of the solenoids 166, 170 will cause movement of the shafts 162, 164 and pivotal movement of the arms 150, 152, 158 and 160. The support portion 144 will thereby be lifted from the base portion 146 (FIG. 9). This will permit insertion of an x-ray cassette 167 for taking x-ray images of the patient. The operation of the solenoids 166, 170 can be controlled by suitable electric control means such as the switch box 174 and the electrical control path 176. The mechanical lifting means can be duplicated on each side of the patient support to provide a uniform lifting action.

This invention can be embodied in other specific forms without departing from the spirit or essential attributes thereof and accordingly, reference should be had to the following claims, rather than to the foregoing specification, as indicating the scope of the invention.

I claim:

1. An assembly for the recordation of an image of a patient cast by x-rays emanating from an x-ray source, said assembly comprising:
   an x-ray cassette for recording said x-ray image;
   a generally flat patient support surface; and,
   a plurality of lifting means disposed about the support surface and adapted to support the patient, said lifting means comprising elongated inflatable runners, and further comprising connection means for placing said elongated inflatable runners in fluid connection with fluid supply means, said connection means further comprising means for selective deflation of said elongated inflatable runners, whereby said elongated inflatable runners, when inflated, support the patient, and whereby selective deflation of the elongated inflatable runners permits the insertion of said x-ray cassette beneath a corresponding portion of the patient for recordation of said x-ray image.

2. The x-ray assembly of claim 1, wherein said support surface includes concave depressions formed in the support surface, one of said elongated inflatable runners being fixed in each of said concave depressions formed in the support surface, said elongated inflatable runners when deflated being collapsible into said depressions to permit insertion of said x-ray cassette.

3. The x-ray assembly of claim 2, wherein said elongated inflatable runners are substantially parallel to one another.

4. The x-ray assembly of claim 2, further comprising at least two substantially parallel head supporting runners, said head supporting runners being aligned substantially perpendicular to the axis of the shoulders of the patient and spaced apart so as to support the head of the patient when said head supporting runners are inflated.

5. The x-ray assembly of claim 1, wherein said connection means for placing said elongated inflatable runners in fluid connection with said fluid supply means comprise at least one valve means.

6. The x-ray assembly of claim 5, further comprising electric actuation means for actuating said valve means.

7. The x-ray assembly of claim 6, further comprising electric control means adapted to control said electric actuation means.

8. The x-ray assembly of claim 7, wherein said electric actuation means comprise a solenoid.

9. The x-ray assembly of claim 1, wherein said connection means for placing said elongated inflatable runners in fluid connection with said fluid supply means comprises a manifold in fluid connection with each of said elongated inflatable runners.

10. An assembly for the recordation of an image of a patient cast by x-rays emanating from an x-ray source, said assembly comprising:
    an x-ray cassette for recording said x-ray image;
    a lower, base portion;
    an upper, support portion, said support portion being substantially separable from and resting on said base portion; and,
    means adapted to lift and separate the support portion from the base portion and to thereby create a space for the insertion of said x-ray cassette between the support portion and the base portion for recordation of said x-ray image.

11. The x-ray assembly of claim 10, wherein said lifting means comprise a plurality of inflatable runners disposed between said support portion and said base portion, and further comprising fluid supply means and connection means for placing said inflatable runners in fluid connection with said fluid supply means, said runners, when inflated, lifting said support portion from said base portion to create a space therebetween for the insertion of said x-ray cassette between said support portion and said base portion, and beneath an adjacent portion of the patient's body.

12. The x-ray assembly of claim 11, wherein said inflatable runners are disposed about the support portion at a distance from one another adapted to permit the insertion of said x-ray cassette therebetween, whereby said inflatable runners will lift an adjacent portion of the patient support and the patient from the base portion and permit the insertion of said x-ray cassette between said support and said base portion, and between said adjacent runners, for recordation of said x-ray image.

13. The x-ray assembly of claim 12, wherein said connection means for placing said inflatable runners in fluid connection with said fluid supply means, and said means for removing fluid from said inflatable runners comprise at least one valve means.

14. The x-ray assembly of claim 12, wherein at least one of said runners is positioned so as to lift the foot of the patient, and other runners are positioned so as to substantially lift the knee area, the pelvis, the upper chest and the head of the patient when said runners are inflated.

15. The x-ray assembly of claim 13, wherein said connection means for placing said inflatable runners in fluid connection with said fluid supply means comprises a manifold in fluid connection with each of said runners.

16. The x-ray assembly of claim 13, further comprising electric actuation means for actuating said valve means and electric control means adapted to control said electric actuation means.

17. The x-ray assembly of claim 16, wherein said electric actuation means comprise a solenoid.

18. The x-ray assembly of claim 11, wherein said inflatable runners are substantially adjacent to one another, and further comprising selective deflation means for deflating particular runners so as to permit the insertion of said x-ray cassette in the space between said support portion and said base portion member created by said deflated runners.

19. The x-ray assembly of claim 18, wherein said connection means for placing said inflatable runners in fluid connection with fluid supply means, and said means for removing fluid from the runners, comprise at least one valve means.

20. The x-ray assembly of claim 19, further comprising electric actuation means for actuating said valves, and electric control means adapted to control said actuation means.

21. The x-ray assembly of claim 20, wherein said electric actuation means comprise a solenoid.

22. The x-ray assembly of claim 10, wherein said lifting means comprise connection means connected to at least one of said support portion and said base portion, said connection means being further connected to means for driving said connection means to lift said support portion from said base portion.

23. The x-ray assembly of claim 22, wherein said connection means comprises pivot arms pivotally connected to at least one of said support portion and said base portion, said pivot arms being further connected to driving means, whereby operation of said driving means will cause pivotal movement of said pivot arms and separation of said support portion from said base portion.

24. The x-ray assembly of claim 11, wherein said elongated inflatable runners comprise lateral elongated inflatable runners and transverse elongated inflatable runners both relative to said support surface, said lateral and transverse elongated inflatable runners being disposed about the support surface to form adjacent quadrangular spaces adapted to receive said x-ray cassette.

25. The x-ray assembly of claim 24, wherein said lateral elongated inflatable runners are selectively deflatable, whereby upon inflation of said elongated inflatable runners, at least one of said lateral elongated inflatable runners can be deflated to permit insertion of the x-ray cassette within a respective quadrangular space without relative movement of a corresponding portion of the patient's body.

* * * * *